US00PP24087P3

(12) United States Plant Patent
Egger

(10) Patent No.: US PP24,087 P3
(45) Date of Patent: Dec. 10, 2013

(54) ***HEUCHERA* PLANT NAMED 'CREOLE NIGHTS'**

(50) Latin Name: ***Heuchera* hybrid**
Varietal Denomination: Creole Nights

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 140 days.

(21) Appl. No.: 13/385,801

(22) Filed: Mar. 6, 2012

(65) Prior Publication Data

US 2013/0239280 P1 Sep. 12, 2013

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — June Hwu

(74) *Attorney, Agent, or Firm* — Klarquist Sparkman, LLP

(57) ABSTRACT

A new and distinct *Heuchera* plant characterized by medium large, glossy near black leaves year round, medium to short, dark peduncles, bicolor pink and white flowers, a well-branched medium-large, mounding habit, and excellent vigor.

1 Drawing Sheet

Botanical denomination: *Heuchera* hybrid.
Variety designation: 'Creole Nights'.

BACKGROUND OF THE INVENTION

The present invention relates to a new and distinct cultivar of *Heuchera* and given the cultivar name of 'Creole Nights'. *Heuchera* is in the family Saxifragaceae. *Heuchera* 'Creole Nights' originated from a cross between *Heuchera* K187-7, a proprietary non-commercial hybrid, as the seed parent, and *Heuchera* K159-1, a proprietary non-commercial hybrid, as, as the pollen parent.

Compared to the seed parent, *Heuchera* K187-7, the new cultivar has glossy near black rather than dull brown leaves.

Compared to the pollen parent, *Heuchera* K159-1, the new cultivar has red black rather than red brown leaves.

Compared to *Heuchera* 'Obsidian', U.S. Plant Pat. No. 14,836, the new cultivar has a larger habit, larger leaves, shorter inflorescences, and larger flowers.

This new *Heuchera* is uniquely distinguished by:

1. medium large, glossy near black leaves year round,
2. medium to short, dark peduncles,
3. bicolor pink and white flowers,
4. well branched, medium large, mounding habit,
5. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a 1-and-a-half-year-old plant of *Heuchera* 'Creole Nights' growing in a two gallon container, grown in a cool greenhouse, in May in Canby, Oreg.

DETAILED PLANT DESCRIPTION

The following is a detailed description of the new *Heuchera* cultivar based on observations taken in April of 2-year-old specimens growing in a two gallon container, grown in a cool greenhouse, in May in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition.

Plant:

*Form.*—Basal rosette, herbaceous perennial.
*Hardiness.*—USDA Zone 4 to 9.
*Size.*—26 cm tall from top of the foliage to the ground and 55 cm wide.
*Habit.*—Mounding.
*Vigor.*—Excellent.

Leaf:

*Type.*—Simple.
*Arrangement.*—Rosette.
*Shape.*—Ovate to orbicular.
*Lobing/division.*—5 to 7 shallow lobes, shallow secondary lobes.
*Venation.*—Palmate.
*Margins.*—Broadly crenate.
*Apex.*—Mucronulate.
*Base.*—Cordate, lobes overlapping at the base.
*Blade size.*—Grows to 13 cm long and 11.5 cm wide.
*Texture.*—Leathery.
*Surface texture.*—Glandular pubescent on both sides.
*Petiole description.*—Grows to 17 cm long and 2.5 mm wide, glandular hairs, Greyed Purple N186B.

*Leaf color.*—Topside, new leaves are Greyed Purple N186B, bottom side Greyed Purple 187A; mature leaves topside are Greyed Purple N186A, bottom side Purple N77A.

Inflorescence:

*Size.*—Grows to 5 cm wide and 9 cm long.

*Type.*—Thyrse.

*Number of flowers per thyrse.*—About 60.

*Number of thyrse.*—About 20 in the first spring flush.

*Peduncle.*—Grows to 28 cm long and 3 mm wide at base, Greyed Purple N186B, glandular hairs.

*Pedicel.*—1.5 mm to 4 mm, with glandular hairs, Greyed Green 195A.

*Bloom period.*—May through October in Canby, Oreg.

Flower bud:

*Size.*—3.5 mm wide and 5 mm long.

*Description.*—Glandular puberulent, ovoid, down facing.

*Color.*—Greyed Purple 186B on the bottom half and White N155A on the top half.

Flower:

*Type.*—Perfect.

*Shape.*—Campanulate.

*Size.*—8 mm long and 5 mm wide.

*Corolla description.*—5 petals, 3 mm long and less than 1 mm wide, spatulate, margins entire, tip acute, glabrous on top and bottom side, White N155B.

*Calyx description.*—Campanulate, 7 mm long and 5 mm wide, with 5 lobes divided ½ way to the base, each 2 mm wide and 3.5 mm long, dense glandular hairs outside and some glandular hairs inside, tip obtuse, margin entire; color both sides Greyed Purple 186B to 186C on bottom half and White N155B on top half.

*Stamen description.*—5 in number, filaments 4 mm long, White N155B, anthers 0.4 mm, Greyed Orange 167B, pollen none.

*Pistil description.*—1, 2-beaked, 7 mm long and 2 mm wide; ovary 2 mm long and 2 mm wide, Yellow Green 152B; style 5 mm long, White NN155B.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

Seed:

*Shape.*—Linear.

*Size.*—2 mm long.

*Color.*—Black 202A.

Pest and disease tolerance: Excellent disease resistance to powdery mildew, the common problem of *Heuchera*. Susceptible to *Heuchera* rust and root weevils.

I claim:

1. A new and distinct *Heuchera* plant as herein illustrated and described.

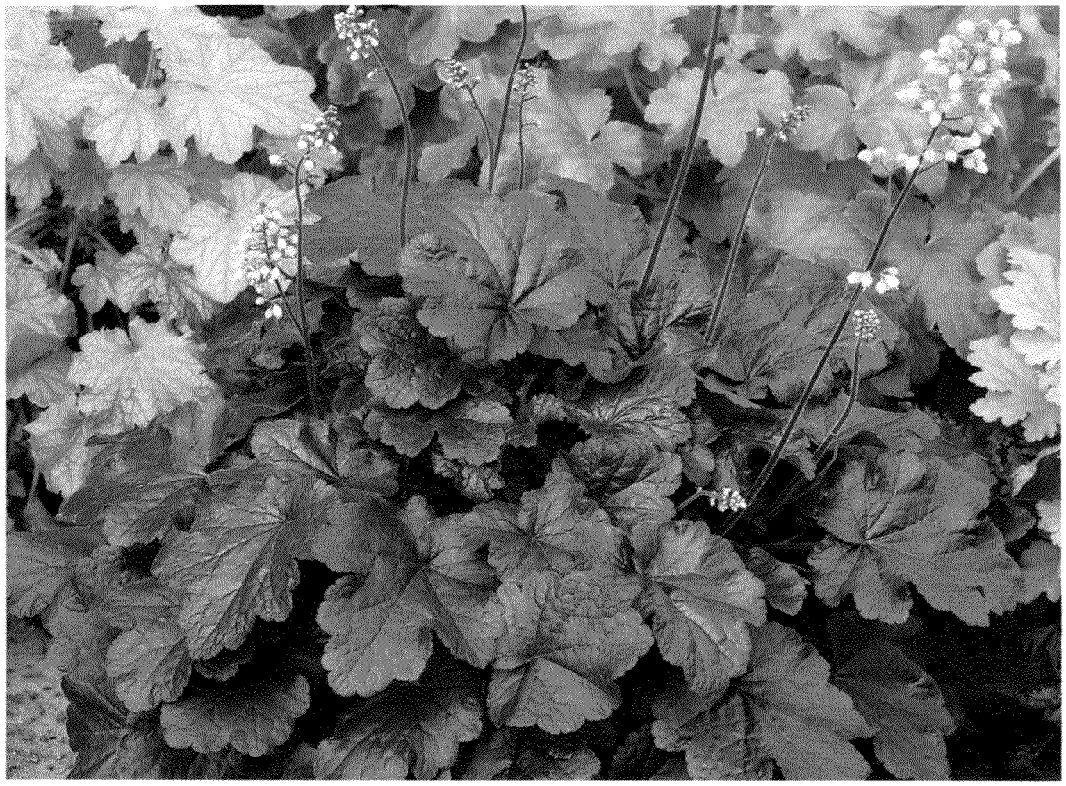

* * * * *